United States Patent [19]

Ottow et al.

[11] Patent Number: 5,405,979
[45] Date of Patent: Apr. 11, 1995

[54] PROCESS FOR THE PRODUCTION OF 10β-H-STEROIDS

[75] Inventors: Eckhard Ottow; Gunter Neef; Arwed Cleve; Rudolf Wiechert, all of Berlin, Germany

[73] Assignee: Schering Aktiengesellschaft, Berlin and Bergkamen, Germany

[21] Appl. No.: 952,739

[22] PCT Filed: Jun. 3, 1991

[86] PCT No.: PCT/EP91/01018
§ 371 Date: Nov. 30, 1992
§ 102(e) Date: Nov. 30, 1992

[87] PCT Pub. No.: WO91/18918
PCT Pub. Date: Dec. 12, 1991

[30] Foreign Application Priority Data

Jun. 1, 1990 [DE] Germany .............. 40 18 167.7

[51] Int. Cl.$^6$ .............. A61K 31/58; C07D 311/96
[52] U.S. Cl. .................................. 552/220
[58] Field of Search .............. 552/220; 514/172, 173

[56] References Cited

U.S. PATENT DOCUMENTS 4,357,278 11/1982 Quinkert et al. .............. 260/397.45

FOREIGN PATENT DOCUMENTS 145493 6/1985 European Pat. Off. .
277676 8/1988 European Pat. Off. .

*Primary Examiner*—Paul J. Killos
*Attorney, Agent, or Firm*—Millen, White, Zelano & Branigan

[57] ABSTRACT

A process for the production of 10β-H-11β-(substituted phenyl) steroids of the formulae Ia or Ib set forth in the claims by reduction of a compound of the formula III:

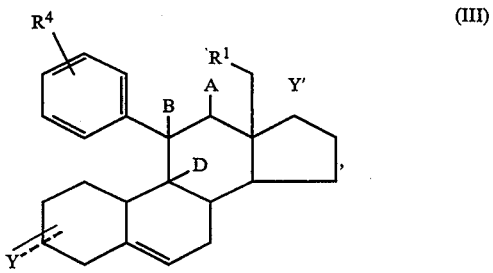

followed by cleaving with a strong acid or partial cleaving with a less strong acid. Reduction with an electropositive metal in an electron-solvating solvent is preferred.

5 Claims, No Drawings

PROCESS FOR THE PRODUCTION OF 10β-H-STEROIDS

This invention relates to a new process for the production of 10β-H-11β-(subst. phenyl) steroids of formula Ia

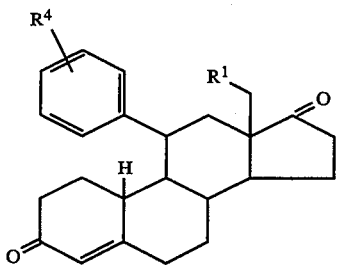
(Ia)

or of formula Ib

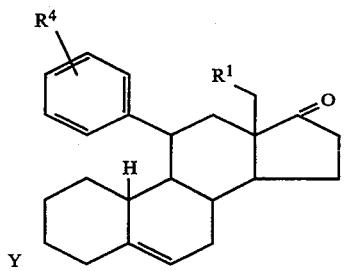
(Ib)

in which $R^4$ stands for a hydrogen atom, a cyano group, a chlorine, fluorine, bromine, iodine atom, for a trialkylsilyl, trialkylstannyl group, for a straight-chain or branched, saturated or unsaturated $C_1$-$C_8$ alkyl, optionally protected acyl or alkoxyalkyl radical, for an amino group

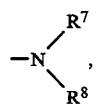

in which $R^7$ and $R^8$, independent of one another, mean a hydrogen atom or a $C_1$-$C_4$ alkyl group or for a corresponding amine oxide

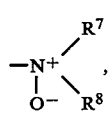

or for the groupings —$OR^9$ or —$S(O)_iR^9$ with i=0, 1 or 2, in which $R^9$ means a hydrogen atom, a methyl, ethyl, propyl, isopropyl, methoxyphenyl, allyl or a 2-dimethylaminoethyl group, or for a heteroaryl radical of formula Iα

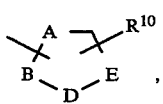
(Iα)

in which A symbolizes a nitrogen, oxygen or sulfur atom, -B-D-E-symbolizes the element sequence —C—C—C—, —N—C—C— or —C—N—C— and $R^{10}$ symbolizes a hydrogen atom, a cyano group, a chlorine, fluorine, bromine, iodine atom, a trialkylsilyl, trialkylstannyl group, a straight-chain or branched, saturated or unsaturated $C_1$-$C_8$ alkyl, optionally protected acyl or alkoxyalkyl radical, an amino group

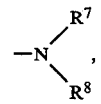

in which $R^7$ and $R^8$, independent of one another, mean a hydrogen atom or a $C_1$-$C_4$ alkyl group, or a corresponding amine oxide

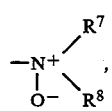

or the grouping —$OR^9$ or —$S(O)_iR^9$ with i=0, 1 or 2 in which $R^9$ means a hydrogen atom, a methyl, ethyl, propyl, isopropyl, methoxyphenyl, allyl or a 2-dimethylaminoethyl group, or for a heteroaryl radical of formula Iβ

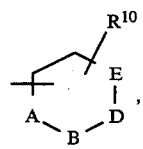
(Iβ)

in which A means a nitrogen atom and -B-D-E- means the element sequence —C—C—C—, —N—C—C—, —C—N—C— —or C—C—N— and $R^{10}$ has the already indicated meaning, or for a phenyl radical of formula Iγ

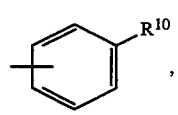
(Iγ)

in which $R^{10}$ has the already indicated meaning,

Y means a protected keto group or a protected hydroxy group and a hydrogen atom as well, $R^1$ means a hydrogen atom or a methyl group.

BACKGROUND OF THE INVENTION

In German patent application P 39 21 059.6, 11β-aryl-4-estrenes of general formula I

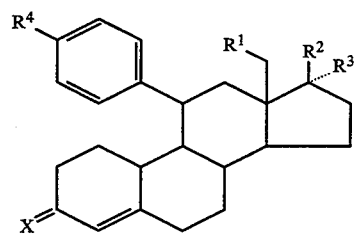
(I)

are described for the first time, in which

X stands for an oxygen atom, the hydroxy imino grouping >N OH or two hydrogen atoms, $R^1$ stands for a hydrogen atom or a methyl group, $R^2$ stands for a hydroxy group, a $C_1$-$C_{10}$ alkoxy or $C_1$-$C_{10}$ acyloxy group, $R^3$ stands for a hydrogen atom, the grouping —$(CH_2)_n CH_2 Z$, in which n is 0, 1, 2, 3, 4 or 5, Z means a hydrogen atom, the cyano group or the radical —$OR^5$ with R=$^5$H, $C_1$-$C_{10}$ alkyl or $C_1$-$C_{10}$ acyl, the grouping —$(CH_2)_m$—C≡C—Y, in which m means 0, 1 or 2 and Y means a hydrogen, fluorine, chlorine, bromine or iodine atom, a $C_1$-$C_{10}$ hydroxyalkyl, $C_1$-$C_{10}$ alkoxyalkyl, $C_1$-$C_{10}$ acyloxyalkyl radical, the grouping —CH=CH—$(CH_2)_k CH_2 R^6$, in which k means 0, 1 or 2 and $R^6$ means a hydrogen atom, a hydroxy group, a $C_1$-$C_4$ alkoxy or $C_1$-$C_4$ acyloxy radical, or else $R^2$ and $R^3$ together stand for a radical of formula

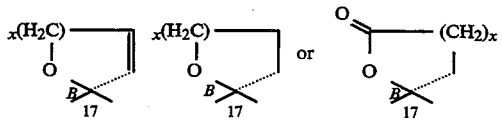

in which x = 1 or 2

$R^4$ stands for a hydrogen atom, for a straight-chain or branched, saturated or unsaturated $C_1$-$C_8$ alkyl, acyl or alkoxyalkyl radical, for an amino group

in which $R^7$ and $R^8$, independent of one another, mean a hydrogen atom or a $C_1$-$C_4$ alkyl group, or for a corresponding amine oxide

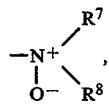

or for the grouping —$OR^9$, in which $R^9$ means a hydrogen atom, a methyl, ethyl, propyl, methoxyphenyl, allyl or a 2-dimethylaminoethyl group, or for a heteroaryl radical of formula Iα

in which A symbolizes a nitrogen, oxygen or sulfur atom, -B-D-E-symbolizes the element sequence —C—C—C—, —N—C—C— or —C—N—C— and $R^{10}$ symbolizes a hydrogen atom, a cyano, trialkylsilyl, trialkylstannyl or amino group

or the radical —$OR^9$ or —$SR^9$ with $R^7$, $R^8$ and $R^9$ in the already indicated meaning, or for a heteroaryl radical of formula Iβ

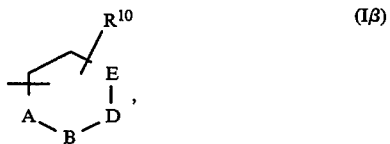

in which A means a nitrogen atom and -B-D-E- means the element sequence of —C—C—C—, —N—C—C—, —C—N—C— or —C—C—N— and $R^{10}$ has the already indicated meaning, or for a phenyl radical of formula Iγ

in which $R^{10}$ has the already indicated meaning, as well as their pharmacologically compatible addition salts with acids.

The new compounds are of great interest first of all because of their strong antigestagen properties. They are produced according to German patent application P 39 21 059.6:

Treatment of compounds of general formula II

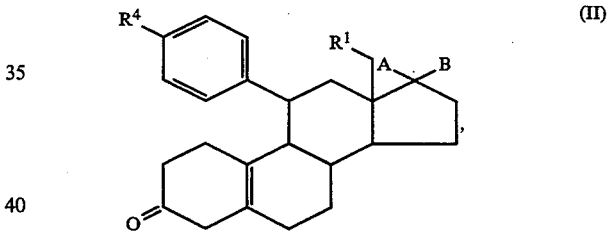

in which $R^1$ and $R^4$ have the meaning indicated in formula I,

A stands for a β-hydroxy group or the radical $R^2$ and B stands for an α-hydrogen atom, an α-position radical $R^3$ or A and B together stand for a keto-oxygen atom, with acid in an inert solvent with heating results in compounds of general formula Ia

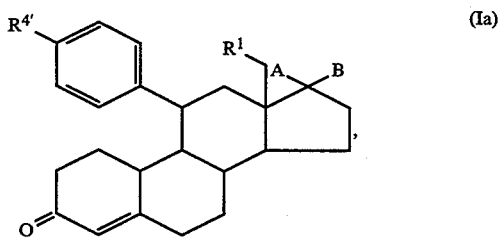

in which $R^1$, A and B have the meaning indicated in formula II and R4' has the same meaning as $R^4$ in formula I, provided that $R^4$ is stable under the above-mentioned drastic reaction conditions.

Preferably for isomerization it is heated to a temperature between 80° and 120° C., namely in an inert solvent such as toluene.

The reaction time is at least 45 minutes, but can, if necessary, be 24 hours or more.

As acids, both mineral and organic acids are suitable; of the latter, p-toluenesulfonic acid is preferred.

In the compounds of general formula Ia, an end compound of general formula I can be involved if substituents $R^4$, A and B in the initial compound of general formula II are those substituents which withstand the drastic reaction conditions necessary for isomerization. In particular, free hydroxy groups on a tertiary carbon atom are eliminated under these reaction conditions.

But it can always be useful to introduce, only after the isomerization, substituents $R^2$ and $R^3$ on the C-17 atom or to synthesize $R^4$ in the 4-position of the 11β-phenyl radical.

Depending on substituents $R^2$, $R^3$ and $R^4$ finally desired in the compound of general formula I, after the isomerization, optionally either a) in the compound of general formula Ia, if A in it stands for a β-hydroxy group and B stands for an α-hydrogen atom, optionally the 17-hydroxy group is oxidized to a 17-keto group and b) the 3-keto function is converted to a dithioketal, and also all other optionally present keto groups are ketalized or else first b) and then a) is performed and then c) in case $R^{4'}$ in the 3-thioketalized compound stands for a methoxy or a hydroxy group and $R^4$ in the finally desired compound of general formula I is not to stand for a methoxy or hydroxy group, the hydroxy compound, optionally after cleavage of the methoxy compound, is converted to a corresponding perfluoroalkylsulfonic acid compound, in which -alkyl- stands for a $C_1$–$C_4$ alkyl radical, and from the latter either directly by reaction with a correspondingly substituted tin(trialkyl) compound $R^{4''}$—Sn(alkyl)$_3$, in which $R^{4''}$ is identical with $R^4$ of general formula I or represents a tautomeric precursor of $R^4$ and -alkyl- means a $C_1$–$C_4$ alkyl radical or indirectly by a compound substituted in 4-position of the 11β-phenyl radical with a tin(trialkyl) radical (alkyl=$C_1$–$C_4$), which was obtained by reaction of the perfluoroalkylsulfonate compound with Sn$_2$alkyl$_6$, and further treatment of the 11β-(4-trialkylstannyl)-phenyl compound with a compound $R^{4''}$—Y, in which $R^{4''}$ is identical with $R^4$ of general formula I or represents a tautomeric precursor of $R^4$ and Y means a leaving group, preferably a halogen atom and especially a bromine atom, in the presence of a transition metal catalyst, a compound of general formula III is produced

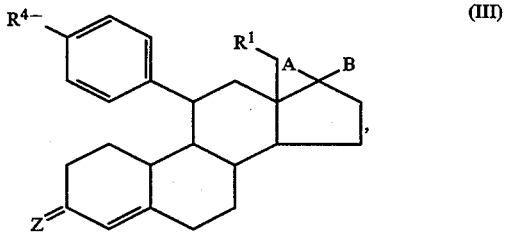

(III)

in which Z means a keto group prospected in the form of a dithioketal, and d) then, if $R^2$ and $R^3$ in the finally desired compound of general formula I are not to stand for a hydroxy group or a hydrogen atom or else $R^2$ and $R^3$ together are not to stand for a keto-oxygen atom, desired substituents $R^2$ and $R^3$ are introduced on a C-17 atom of the steroid skeleton according to methods known in the art or else first d) and then c) is performed, protecting groups are cleaved, optionally free hydroxy groups are alkylated or acylated and optionally with hydroxylamine hydrochloride, the 3-keto group is converted to a 3-hydroxyimino grouping >N~OH or the 3-keto group is converted to the dihydro compound as well as optionally a pharmaceutically compatible addition salt is produced with an acid.

The performance of process steps a), b), c) and d) takes place according to methods known in the art.

Oxidation a) of the hydroxy to keto group can be performed, for example, according to Oppenauer or with chromic acid reagents (Jones reagent) or chromic acid-pyridine.

As a protecting group for the 3-keto function, preferably the ethane-1,2-diyl-bis(thio) group is used, which can be introduced on the steroid-3-C atom by reaction of the 3-keto compound with ethane-1,2-dithiol in the presence of, e.g., p-toluenesulfonic acid.

To protect the keto group of the acyl group possible in $R^4$, the ethylenedioxy or 2,2-dimethylpropylene-1,3-dioxy group is suitable. Also, other standard protecting groups are possible.

Alternatively, first the oxidation and then the protecting group introduction or else first the protecting group introduction and then the oxidation can be performed.

Reaction step c) is used for the synthesis of substituents $R^4$ or $R^{4'}$ in p-position on the 11β-phenyl ring. This process is then necessary if $R^4$ represents a substituent which does not withstand the drastic isomerization conditions, for example, an allyl or vinyl radical.

The 11β-(4-hydroxyphenyl) compound, which is obtainable from the corresponding methoxy compound by ether cleavage, for example, with sodium methanethiolate in a solvent such as dimethylformamide, is used as a starting point for this synthesis.

By reaction of the hydroxy compound with a perfluoro-($C_1$–$C_4$)-alkylsulfonic acid anhydride or halide in the presence of a base such as pyridine or 4-(dimethylamino)-pyridine, the corresponding 11β-[4-(perfluoroalkylsulfonyloxy)phenyl] compound is attained (P. J. Stang, M. Hanack and L. R. Subramanian, *Synthesis* 85, (1982)).

In this case, the process is performed either so that in a transition metal-catalyzed reaction (preferably Pd$^o$), the perfluoroalkylsulfonate leaving group with basically almost simultaneous substitution is displaced by the desired substituent or its precursor (J. E. McMurry and S. Mohanraj, Tetrahedron Letters, 24, No. 27, pp. 2723–2726, 1983; X. Lu and J. Zhu, Communications, pp. 726–727, 1987; Q. -Y. Chen and Z. -Y. Yang, Tetrahedron Letters 27, No. 10, pp. 1171–1174, 1986; S. Cacchi, P. G. Ciattini, F. Morera and G. Ortar, Tetrahedron Letters, 27, No. 33, pp. 3931–3934, 1986; A. M. Echavarren and J. K. Stille, J. Am. Chem. Soc. 1987, 109, pp. 5478–5486) or a corresponding tri-organylstannyl, preferably tri-n-alkylstannyl compound is produced intermediately and transition metal-catalyzed from the perfluroroalkylsulfonate compound [J. K. Stille, Angew. Chem. [Appl. Chem.], pp. 504–519]. This is then reacted in a one-pot process with a halogen, preferably bromine- or iodine-substituted carbocyclic or heterocyclic aromatic compound [Y. Yamamoto, Y. Azuma, H. Mitoh, Communications, pp. 546–565, 1986; T. J. Bailey, Tetrahedron Letters, 27, No. 37, pp. 4407–4410, 1986], which optionally can have still other substituents; the 11β-phenyl radical then exhibits in it the desired substitution or a precursor of the desired substitution,.

Numerous such reactions with steroids, in which a trifluoromethanesulfonate group is in 4-position of an 11β-phenyl ring, are described in EP-A-0283428.

Free hydroxy groups can be alkylated or acylated in a way known in the art.

Dialkylamines can be converted by suitable oxidizing agents (e.g., hydrogen peroxide or peracids) to the desired N oxides [see, e.g., Kontakte [Contacts] (Darmstadt) 1986, 3, p. 12].

Compounds with a dialkylamine substituent on the 11β-phenyl ring can be converted by reaction with bromocyanogen in aprotic solvents such as, for example, dioxane, benzene or toluene at increased temperature (amine catabolism according to Braun) analogously to the instructions indicated, for example, in Org. Reactions 7, 198 (1953), K. W. Bentley, Techniques of Organic Chemistry 11, 773 (1963) and Houben-Weyl, 5/4, 151 (1960) in good yield to the corresponding (N-cyano-N-alkylaminoaryl)-derivatives.

The latter are reduced depending on the finally desired meaning of

in the end product in a way known in the art to the corresponding dialkylamine compounds (for example, with diisobutyl aluminum hydride in toluene to the N-formyl-N-alkylaminophenyl intermediate products and then with lithium aluminum hydride) or N—H—N-alkyl compounds (for example, with lithium aluminum hydride or with lithium in liquid ammonia). The latter are then optionally acylated in a way known in the literature and optionally then reduced to the new dialkylamine derivative in a known way with, for example, lithium aluminum hydride (see DE 36 23 038).

In process step d), substituents $R^2$ and $R^3$ finally desired on the 17-C atom finally are introduced, unless a methoxy or hydroxy group already comprised from the start as $R^2$ or a hydrogen atom as $R^3$ or a keto-oxygen atom formed together from $R^2$ and $R^3$ is involved. This introduction takes place analogously to processes known in the literature (for example, J. Fried, J. A. Edwards, "Organic Reactions in Steroid Chemistry," Van Nostrand Reinhold Company, 1972, Vol. 1 and 2; "Terpenoids and Steroids," Specialist Periodical Report, The Chemical Society, London, Vol. 1–12) by nucleophilic addition to the C-17 ketone.

Detailed data in this connection is found in German patent application P 39 21 059.6 and in corresponding European patent application EP-A-0404283.

SUMMARY OF THE INVENTION

It has now been found that the compounds of general formulas Ia and Ib, which are suitable as initial products for the production of the 10β-H steroids of general formula I, can easily be produced by a compound of formula III

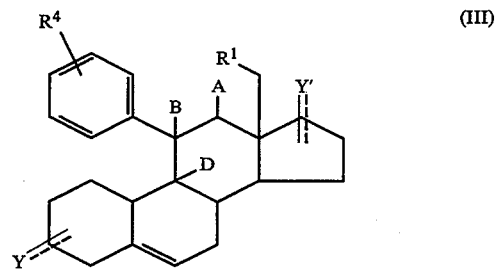

in which

A and B together mean an additional bond and
D means a hydrogen atom or
B and D together mean an additional bond and
A means a hydrogen atom and
$R^4$, Y, Y' as well as $R^1$ have the meaning indicated in formulas Ia or Ib, being reduced without destruction of the aromatic system and the 5,6-double bond to a compound of general formula IIa

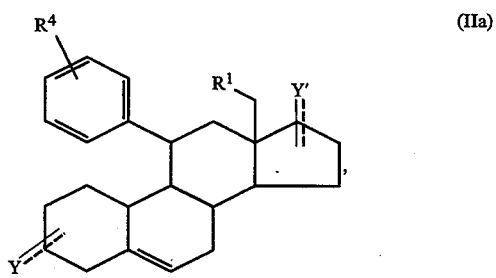

in which $R^4$, Y, Y' and $R^1$ have the already indicated meaning and then optionally this compound of general formula II being cleaved either with a strong acid to a compound of general formula Ia or with a less strong acid partially to a compound of general formula Ib.

In the reduction of III, the 11β-aryl compound IIa (stereoselective reduction) is formed.

To reduce the 9(11) or 11(12) double bond in III, various methods are suitable according to the invention:

The reduction with an electropositive metal in an electron-solvating solvent or in a solvent containing a solubilizer is preferred according to the invention. As an electron-solvating solvent, first of all ammonia is suitable.

Equimolar amounts of reducing agent are sufficient for the reduction, however, a considerable excess of reducing agent can also be used without the aromatic system and/or the 5,6-double bond being attacked.

As electropositive metals, all metals suitable for a Birch reduction are usable. According to the invention, lithium, potassium, sodium and calcium—and of these, especially lithium—are preferred.

This invention also relates to the compounds of general formulas IIa, Ia and Ib. They can be further processed to the valuable end products of general formula I in the way indicated in P 39 21 059.6.

The protected keto groups of the compounds of general formula IIa that have developed in the Birch reduction can be cleaved successively depending on the intended further processing.

If the 4-aryl substituent in the compound of general formula IIa already corresponds to substituent $R^4$ in the end product of formula I, the keto protecting group in 17-position is first cleaved with a weak acid (acetic acid, oxalic acid), substituents R² and R³ are introduced and then the protecting group in 3-position is separated with a strong acid. As strong acids, for example, hydrochloric acid, sulfuric acid, phosphoric acid or toluenesulfonic acid can be mentioned. Then, still other reactions for the functionalization can follow, for example, the hydrogenation of a C—C-triple to a C—C-double bond.

If the 4-aryl substituent stands for a methoxy group and in the end product of general formula I is to have another meaning, action is taken so that on the 11β-phenyl radical, first finally desired substituent R⁴ as described in P 39 21 059.6 is synthesized, then the 17-keto group is released, R² and R³ are introduced and then the 3-keto protecting group is cleaved. This process is then applied when substituent R⁴ cannot easily be quasi "co-introduced" on the aromatic compound already in the production of the initial product of general formula III.

Treatment of a compound of general formula IIa with a strong acid leads directly to the corresponding 3,17-diketone of general formula Ia.

From a compound of general formula Ia, a compound of general formula III can be produced by thioketalization according to standard methods, which is necessary for the process described in P 39 21 059.6.

It is also possible to produce the 4-hydroxyaryl compounds from the 4-methoxy-substituted aryl compound of general formula IIa, optionally after selective removal of the 17-keto protecting group, to convert the 4-hydroxyaryl compounds to the corresponding perfluoroalkylsulfonyloxy compound, to introduce the latter in the way already described above either directly by transition-metallized coupling with a corresponding compound of general formula IV comprising radical R⁴

$$R^4-K \qquad (IV),$$

in which R⁴ has the meaning finally desired for this substituent in formula Ia, Ib or IIa and K stands for one of the radicals

| —B (alkyl)₂ | |
| —Sn (alkyl)₃ | alkyl = C₁–C₄ alkyl radical |
| —B (OH)₂ | |
| —ZnHal | Hal = Cl, Br, I |
| —MgHal | | or to introduce finally desired radical R⁴ indirectly by the 4-(trialkyltin)-aryl compound produced with hexabutylditin and then to cleave off still existing protecting groups.

By subsequent thioketalization, initial compounds suitable for the process described in P 39 21 059.6 again are achieved.

The production of the initial products of general formula III (for R⁴=OCH₃) to be used according to the invention can be seen from subsequent examples Ia), IIa), and Ib), IIb).

By variation of the substituent on the phenyl ring of the phenylboronic acid used for coupling with the (11-trifluoromethylsulfonyloxy)-substituted steroid, other compounds of general formula III can be produced in an analogous way (Y. Hoshino, N, Miyaura and A. Suzuki, Bull. Chem. Soc., Jpn. 61, 3008 (1988); H. Matsubasa, K. Seto, T. Tahara and S. Takahashi, Bull. Chem. Soc. Jpn. 62, 3896 (1989).

The following examples are used for a more detailed explanation of the invention:
Experimental part:

I) Production of the initial products
  a) 3,3;17,17-Bis-(ethylenedioxy)-11-trifluoromethylsulfonyloxy-5,9(11)-estradiene 26.1 g (69.7 mmol) of 3,3;17,17-bis-(ethylenedioxy)-5-estren-11-one is dissolved in 350 ml of absolute methylene chloride and mixed under protective gas with 18 ml of 2,6-di-tert-butyl pyridine After cooling of this solution to 0° C., 12.9 ml (76.8 mmol) of trifluoromethanesulfonic acid anhydride is slowly instilled. Then, the reaction mixture is stirred for 20 more hours at room temperature. For working up, it is poured on saturated sodium bicarbonate solution, the organic phase is separated and the aqueous phase is subsequently extracted with methylene chloride. The combined organic phases are washed with saturated sodium chloride solution, dried on sodium sulfate and concentrated by evaporation in a vacuum. After chromatography of the crude product on silica gel with a mixture of ethyl acetate/hexane, besides 16.4 ml of 2,6-di-tert-butyl pyridine and 5.1 g of 3,3;17,17-bis-(ethylenedioxy)-5-estren-11-one, 27 g of 3,3;17,17-bis-(ethylenedioxy)-11-trifluoromethylsulfonyloxy-5,9(11)-estradiene is obtained as white foam.

$[\alpha]^{20}_D = +104°$ (CHCl₃; c=0.505)
¹H-NMR(CDCl₃) δ: 5.58 ppm (1H,d broad J=5 Hz,H-6); 3.7–4.0 ppm (8H,m,H-ketals); 2.88 ppm (1H,d broad J=11 Hz,H-10); 2.74 ppm (1H,dtr J=16 Hz and J=2.5 Hz,H-12); 2.18–2.33 ppm (2H,m,H-4); 0.84 ppm (3H,s,H-18).

b) 3,3;17,17-Bis-(ethylenedioxy)-11-trifluoromethylsulfonyloxy-5,11-estradiene 11.2 ml (80.1 mmol) of diisopropylamine is introduced at −30° C. in 260 ml of absolute tetrahydrofuran under protective gas and mixed with 1.8 ml of a 1.6 molar n-butyllithium solution in hexane. Then, the solution is stirred for one hour at 0° C. After instillation of a solution of 10 g of 3,3;17,17-bis-(ethylenedioxy)-5-estren-11-one in 130 ml of absolute tetrahydrofuran, it is stirred for deprotonation for 45 more minutes at 0° C., then the reaction mixture is cooled down to −78° C. and mixed with 13 ml of trifluoromethanesulfonic acid anhydride by slow instillation. After 2.5 more hours of stirring at −78° C., the reaction mixture is poured on saturated sodium bicarbonate solution and the aqueous phase is extracted with ethyl acetate. The combined organic phases are washed with saturated sodium chloride solution, dried on sodium sulfate and concentrated by evaporation in a vacuum. After chromatography of the crude product on silica gel with a mixture of ethyl acetate/hexane, besides 2.4 g of 3,3;17,17-bis-(ethylenedioxy)-5-estren-11-one, 5.9 g of 3,3;17,17-bis-(ethylenedioxy)-11-trifluoromethylsulfonyloxy-5,11-estradiene is obtained as white foam.

Melting point=128°–129° C. (diisopropyl ether); $[\alpha]^{20}_D = −31°$ (CHCl₃; c=0.505)

II) Introduction of the 11-aryl substituent by catalytic coupling
  a) 3,3;17,17-Bis-(ethylenedioxy)-11-(4-methoxyphenyl)-5,9(11)-estradiene 21.6 g (42.6 mmol) of 3,3;17,17-bis-(ethylenedioxy)-11-trifluoromethylsulfonyloxy-5,9(11)-estradiene is dissolved in a mixture of 360 ml of toluene and 170 ml of ethanol and mixed in succession with 2.5 g of palladium-tetrakistriphenylphosphine, 3.6 g of lithium chloride, 55 ml of 2 molar sodium carbonate solution and 7.2 g (46.8 mmol) of 4-methoxyphenyl boronic acid. The reaction mixture is then stirred for two hours at 95° C., cooled to room temperature and mixed with saturated sodium chloride solution. The organic phase is separated, washed in succession with 5% sodium hydroxide solution and water, dried on sodium sulfate and concentrated by evaporation in a vacuum. The residue is chromatographed on silica gel with a mixture of ethyl acetate/hexane. 19.2 g of the title compound is obtained as white foam.

By way of example, the representation of several other products is indicated analogously to the above instructions in the table below:

| Aromatic compound | Product | Yield | Physical Data |
|---|---|---|---|
| 4-methoxy-phenyl-boronic acid | 3,3;17,17-bis-(ethylenedioxy)-11-(4-methoxyphenyl)-5,9(11)-estradiene | 97 | mp = 156° C. (diisopropyl ether) $[\alpha]_D^{20} = -0.1°$ (CHCl$_3$; c = 0.52) |
| 4-methyl-phenyl-boronic acid | 3,3;17,17-bis-(ethylenedioxy)-11-(4-methylphenyl)-5,9(11)-estradiene | 92 | mp = 175° C. (diisopropyl ether) $[\alpha]_D^{20} = -11°$ (CHCl$_3$; c = 0.505) |
| phenyl-boronic acid | 3,3;17,17-bis-(ethylenedioxy)-11-phenyl-5,9(11)-estradiene | | mp = 189° C. (diisopropyl ether) $[\alpha]_D^{20} = -3°$ (CHCl$_3$; c = 0.5) |
| 4-bromo-phenyl-boronic acid | 3,3;17,17-bis-(ethylenedioxy)-11-(4-bromophenyl)-5,9(11)-estradiene | 62 | mp = 171° C. (diisopropyl ether) $[\alpha]_D^{20} = -15°$ (CHCl$_3$; c = 0.5) |
| 4-(dimethylamino)-phenyl-boronic acid | 3,3;17,17-bis-(ethylenedioxy)-11-[4-(dimethylamino)phenyl]-5,9(11)-estradiene | 98 | mp = 211° C. (diisopropyl ether) $[\alpha]_D^{20} = -48°$ (CHCl$_3$; c = 0.52) | b)   3,3;17,17-Bis-(ethylenedioxy)-11-(4-methylphenyl)-5,11-estradiene 1.7 g (3.4 mmol) of 3,3;17,17-bis-(ethylenedioxy)-11-trifluoromethylsulfonyloxy-5,11-estradiene is dissolved in a mixture of 31 ml of toluene and 14 ml of ethanol and mixed in succession with 0.2 g of palladiumtetrakistriphenylphosphine, 0.29 g of lithium chloride, 4.4 ml of 2 molar sodium carbonate solution and 0.5 g (3.7 mmol) of 4-methylphenylboronic acid. The reaction mixture is then stirred for 1 hour at 95° C., cooled to room temperature and mixed with saturated sodium chloride solution. The organic phase is separated, washed in succession with 5% sodium hydroxide solution and water, dried on sodium sulfate and concentrated by evaporation in a vacuum. The residue is chromatographed on silica gel with a mixture of ethyl acetate/hexane. 1.28 g of the title compound is obtained as white foam.

By way of example, the representation of several other products is indicated in the table below analogously to the above instructions:

| Aromatic compound | Product | Yield % | Physical Data |
|---|---|---|---|
| 4-methyl-phenyl-boronic acid | 3,3;17,17-bis-(ethylenedioxy)-11-(4-methylphenyl)-5,11-estradiene | 88 | mp = 152° C. (diisopropyl ether) $[\alpha]_D^{20} = +20°$ (CHCl$_3$; c = 0.505) |
| 4-methoxy-phenyl-boronic acid | 3,3;17,17-bis-(ethylenedioxy)-11-(4-methoxyphenyl)-5,11-estradiene | 92 | mp = 148° C. (diisopropyl ether) $[\alpha]_D^{20} = +22°$ (CHCl$_3$; c = 0.505) |
| phenyl-boronic acid | 3,3;17,17-bis-(ethylenedioxy)-11-phenyl-5,11-estradiene | 91 | $^1$H-NMR(CDCl$_3$) δ [ppm]: 7.12–7.4 (5H,m,H-aromatic); 5.7 (1H,d J=1Hz, H-12); 5.6 (1H, d J=5Hz broad, H-6); 1.0 (3H,s,H-18) |
| 4-bromo-phenyl-boronic acid | 3,3;17,17-bis-(ethylenedioxy)-11-(4-bromophenyl)-5,11-estradiene | 65 | $^1$H-NMR (CDCl$_3$) δ: [ppm]: 7.37 (2H,d J=8.5Hz,H-aromatic); 7.05,(2H,d=8.5Hz,H-aromatic); 5.72 (1H,d J=1Hz,H-12); 5.59 (1H,d J=5Hz broad,H-6); 0.96 (3H,s,H-18) |

3,3;17,17-Bis-(ethylenedioxy)-11β-(4-methoxyphenyl)-5-estrene 800 ml of ammonia is condensed at −70° C. and mixed with 1.39 g of lithium. After occurrence of the characteristic blue coloring, 18.6 g (40 mmol) of 17,17-bis-(ethylenedioxy)-11-(4-methoxyphenyl)-5,9(11)-estradiene dissolved in 400 ml of tetrahydrofuran is instilled. After 20 more minutes of stirring, the excess lithium is decomposed by the addition of water, the ammonia evaporates, the reaction mixture is poured on saturated ammonium chloride solution and the aqueous phase is extracted with ethyl acetate. The combined organic phases are washed with saturated sodium chloride solution, dried on sodium sulfate and concentrated by evaporation in a vacuum. After chromatography of the crude product on silica gel with a mixture of ethyl acetate/hexane, 15.2 g of 3,3;17,17-bis-(ethylenedioxy)-11β-(4-methoxyphenyl)-5-estrene and 1.4 g of 17,17-bis-(ethylenedioxy)-11-(4-hydroxyphenyl)-5,9(11) -estradiene* are isolated as white foams.

*Melting point=168°–170° C. (ethyl acetate); $[\alpha]_D^{20} = -11°$ (CHCl$_3$; c=0.505)

By way of example, the representation of several other products is indicated analogously to the above instructions in the table below:

| Product | Yield % | Physical Data |
|---|---|---|
| 3,3;17,17-bis-(ethylenedioxy)-11β-(4-methoxyphenyl)-5-estrene | 81 | mp = 187–188° C. (diisopropyl ether) $[\alpha]_D^{20} = +2°$ (CHCl$_3$; c = 0.51) |
| 3,3;17,17-bis-(ethylenedioxy)-11β-(4-methyl- | 89 | mp = 200–201° C. (diisopropyl ether) |

| Product | Yield % | Physical Data |
|---|---|---|
| phenyl)-5-estrene | | $[\alpha]_D^{20}$ = +10° (CHCl$_3$; c = 0.375) |
| 3,3;17,17-bis-(ethylene-dioxy)-11β-[4-(2-propenyl)-phenyl]-5-estrene | 85 | $^1$H-NMR(CDCl$_3$) δ [ppm]: 7.25 (2H,d J= 9.5Hz,H-aromatic); 7.04 (2H,d J= 9.5Hz,H-aromatic); 5.9–6.07 (1H,m,H-CH= ); 5.53 (1H,d J= 5Hz broad,H-6); 5.0–5:1 (2H,m,H-CH$_2$=) ;3.42 (1H,t J= 5.5Hz broad, H-11); 3.34 (2H,d J= 6Hz,H—CH$_2$—Ar); 0.56 (3H,s,H-18) |
| 11β-[4-(dimethyl-amino)-phenyl]-3,3;17,17-bis-ethylenedioxy)-5-estrene | 96 | $^1$H-NMR(CDCl$_3$) δ [ppm]: 7.19 (2H,d J= 9Hz,H-aromatic); 6.64 (2H,d J= 9Hz,H-aromatic); 5.53 (1H,m,H-6); 3.36 (1H,t J= 5.5Hz broad,H-11); 2.92 (6H,s,H-NMe$_2$) 2.41 (1H,m,H-10); 0.60 (3H,s,H-18) |

11β-(4-Methoxyphenyl)-4-estrene-3,17-dione 1 g of 3,3;17,17-bis-(ethylenedioxy)-11β-(4-methoxyphenyl)-5-estrene is dissolved in 50 ml of acetone and mixed under protective gas with 2.5 ml of 4 n aqueous hydrochloric acid. After three hours of stirring at room temperature and one hour at 40° C., the reaction mixture is poured on cold saturated sodium bicarbonate solution and the aqueous phase is extracted several times with methylene chloride. The combined organic phases are dried on sodium sulfate and concentrated by evaporation in a vacuum. The residue is chromatographed on silica gel-with a mixture of ethyl acetate/hexane. 683 mg of 11β-(4-methoxyphenyl)-4-estrene-3,17-dione is obtained as white foam.

Melting point=155°–156° C. (diisopropyl ether); $[\alpha]_D^{20}$=+169° (CHCl$_3$; c=0.505)

3,3-(Ethylenedioxy)-11β-(4-methoxyphenyl)-5-estren-17-one 14 g of silica gel is suspended in 30 ml of methylene chloride, mixed with 1.4 ml of saturated oxalic acid solution and stirred for 15 more minutes. 4.67 g (10 mmol) of 3,3;17,17-bis-(ethylenedioxy)-11β-(4-methoxyphenyl)-5-estrene is added to this suspension and the reaction mixture is stirred at room temperature for 4 more hours. Then, it is suctioned off on a frit, the frit residue is rewashed with methanol/methylene chloride and the thus obtained filtrate is shaken out with saturated sodium bicarbonate solution. The organic phase is dried on sodium sulfate and concentrated by evaporation in a vacuum. The residue is chromatographed on silica gel with a mixture of ethyl acetate/hexane. 3.28 g of 3,3-(ethylenedioxy)-11β-(4-methoxyphenyl)-5-estren-17-one is obtained as white foam.

Corresponding to the table below, other products can also be produced analogously to the above instructions:

| Product | Yield % | Physical Data |
|---|---|---|
| 3,3-(ethylenedioxy)-11β-(4-methoxyphenyl)-5-estren-17-one | 78 | mp = 223° C. (ethyl acetate) $[\alpha]_D^{20}$ = +90° (CHCl$_3$; c = 0.505) |
| 3,3-(ethylenedioxy)-11β-(4-methylphenyl)-5-estren-17-one | 81 | mp = 165–166° C. (diisopropyl ether) $[\alpha]_D^{20}$ = +98° (CHCl$_3$; c = 0.515) |
| 3,3-(ethylenedioxy)-11β-[4-(2-propenyl)phenyl]-5-estren-17-one | 78 | mp = 163–165° C. (diisopropyl ether) $[\alpha]_D^{20}$ = +90° (CHCl$_3$; c = 0.505) |

11β-[4-(Dimethylamino)phenyl]-3,3-(ethylenedioxy)-5-estren-17-one 15 g of silica gel is suspended in 25 ml of dichloromethane, mixed with 4 ml of 3 molar hydrochloric acid and stirred for 15 more minutes. A solution of 5.0 g of 11β-[4(dimethylamino)phenyl]-3,3;17,17-bis-(ethylenedioxy)-5-estrene in 26 ml of dichloromethane is added to this suspension and the reaction mixture is stirred at room temperature for 3 more hours. Then, it is suctioned off on a frit, the frit residue is rewashed with methanol/dichloromethane and the thus obtained filtrate is shaken out with saturated sodium bicarbonate solution. The organic phase is dried on sodium sulfate and concentrated by evaporation in a vacuum. The residue is chromatographed on silica gel with a mixture of ethyl acetate/hexane. 2.21 g of the title compound is obtained as white foam.

Melting point=238°–140° C. (hexane/ethyl acetate); IR (KBr): 1738 cm$^{-1}$ (C=O)

3,3-(Ethylenedioxy)-11β-(4-methylphenyl)-17-[3-(tetrahydro-2H-pyran-2-yloxy)prop-1-inyl]-5-estren-17β-ol 11.2 ml of 2-[(2-propinyl)oxy]tetrahydro-2H-pyran is introduced in 360 ml of absolute tetrahydrofuran at 0° C. and then mixed with 45 ml of a 1.6 molar n-butyllithium solution in hexane slowly without a great temperature increase. After 15 more minutes of stirring, a solution of 3 g of 3,3-(ethylenedioxy)-11β-(4-methylphenyl)-5-estren-17-one, dissolved in 72 ml of absolute tetrahydrofuran, is instilled slowly with ice bath cooling in this reaction mixture and allowed to stir for 60 more minutes. Then, the reaction mixture is poured on water, the aqueous phase is extracted with ethyl acetate and the organic phase is washed with sodium chloride solution. After drying on sodium sulfate and concentration by evaporation of the organic phase in a vacuum, the residue is chromatographed on aluminum oxide (neutral, stage III). 3.68 g of 3,3-(ethylenedioxy)-11β-(4-methylphenyl)-17-[3-(tetrahydro-2H-pyran-2-yloxy)-prop-1-inyl]-5-estren-17β-ol is obtained as white foam.

IR (KBr): 2240 cm$^{-1}$

17β-Hydroxy-11β-(4-methylphenyl)-17-(3-hydroxyprop-1-inyl)-4-estren-3-one 3.42 g of 3,3-(ethylenedioxy)-11β-(4-methylphenyl)-17-[3-(tetrahydro-2H-pyran-2-yloxy)prop-1-inyl]-5-estren-17β-ol is dissolved in 150 ml of acetone and mixed under protective gas with 7.5 ml of 4 molar aqueous hydrochloric acid. After three hours of stirring at room temperature and one hour at 40° C., the reaction mixture is poured on cold, saturated sodium bicarbonate solution and the aqueous phase is extracted several times with methylene chloride. The combined organic phases are dried on sodium sulfate and concentrated by evaporation in a vacuum. The residue is chromatographed on silica gel with a mixture of ethyl acetate/hexane. 2.1 g of 17β-hydroxy-11β-(4-methylphenyl)-17-

(3-hydroxyprop-1-inyl)-4-estren-3-one is obtained as yellowish foam.

$[\alpha]_D^{22} = -26.6°$ (CHCl$_3$; c=0.500)

$^1$H-NMR(CDCl$_3$) δ: 7.29 ppm (2H,d J=8.0 Hz,H-aromatic); 7.09 ppm (2H,d J=8.0 Hz,H-aromatic); 5.86 ppm (1H,s broad,H-4); 4.37 ppm (2H,m,H—CH$_2$O); 3.39 ppm (1H, dd broad,J=6.5 Hz and J=5.0 Hz,H-11); 2.85 ppm (1H,m,H-10); 2.32 ppm (3H,s,H—CH$_3$); 0.76 ppm (3H,s,H-18).

17β-Hydroxy-11β-(4-methylphenyl)-17-(3-hydroxyprop-1-(Z)-enyl)-4-estren-3-one 2 g of 17β-hydroxy-11β-(4-methylphenyl)-17-(3-hydroxyprop-1-inyl)-4-estren-3-one is dissolved in 50 ml of tetrahydrofuran, mixed with 2 ml of pyridine and, by using 200 mg of palladium (10%), hydrogenated on barium sulfate as catalyst at standard pressure. After absorbing an equivalent of hydrogen, the reaction mixture is filtered on Celite, the filter residue is rewashed with ethyl acetate and the filtrate is concentrated by evaporation in a vacuum. The residue is chromatographed on silica gel with a mixture of hexane/ethyl acetate, and 1.72 g of 17β-hydroxy-11β-(4-methylphenyl)-17-(3-hydroxyprop-1-(Z)-enyl)-4-estren-3-one is obtained as white foam.

$[\alpha]_D^{22} = +75.8°$ (CHCl$_3$; c=0.510)

$^1$H-NMR(CDCl$_3$) δ: 7.29 ppm (2H,d J=8.0 Hz,H-aromatic); 7.09 ppm (2H,d J=8.0 Hz,H-aromatic); 5.85 ppm (1H,s broad,H-4); 5.71 ppm (1H,ddd J=12.0 Hz and J=5.5 Hz and J=5.5 Hz,H—CH=); 5.62 ppm (1H,d broad J=12.0 Hz,H—CH=); 4.24 ppm (2H,m,H—CH$_2$O); 3.33 ppm (1H,dd broad J=6.0 Hz and J=5.0 Hz,H-11); 2.84 ppm (1H,m,H-10); 2.32 ppm (3H,s,H—CH$_3$); 0.71 ppm (3H,s,H-18).

3,3;17,17-Bis-(ethylenedioxy)-11β-(4-hydroxyphenyl)-5-estrene 9.33 g of 3,3;17,17-bis-(ethylenedioxy)-11β-(4-methoxyphenyl)-5-estrene is dissolved in 100 ml of absolute dimethylformamide, mixed with 5.6 g of sodium methanethiolate and the reaction mixture is refluxed for 3 hours. After cooling, it is poured on water and the aqueous phase is extracted with ethyl acetate. The combined organic phases are washed several times with saturated sodium chloride solution, dried on sodium sulfate and concentrated by evaporation in a vacuum. The residue is chromatographed on silica gel with a mixture of ethyl acetate/hexane and 8.67 g of 3,3;17,17-bis-(ethylenedioxy)-11β-(4-hydroxyphenyl)-5-estrene is obtained as white foam.

Melting point=224°-225° C. (diisopropyl ether); $[\alpha]_D^{20} = +1.5°$ (CHCl$_3$; c=0.505)

3,3-(Ethylenedioxy)-11β-(4-hydroxyphenyl)-5-estren-17-one a) Analogously to the above instructions for methyl ether cleavage, 1.83 g of 3,3-(ethylenedioxy)-11β-(4-hydroxyphenyl)-5-estren-17-one is obtained as white foam from 3 g of 3,3-(ethylenedioxy)-11β-(4-methoxyphenyl)-5-estren-17-one.

b) Analogously to the above instructions for selective ketal cleavage, 453 mg of 3,3-(ethylenedioxy)-11β-(4-hydroxyphenyl)-5-estren-17-one is obtained as white foam from 0.6 g of 3,3;17,17-bis-(ethylenedioxy)-11β-(4-hydroxyphenyl)-5-estrene.

Melting point=315°-317° C. with decomposition (methylene chloride); $[\alpha]_D^{20} = +93°$ (CHCl$_3$; c=0.515)

3,3-(Ethylenedioxy)-11β-(4-trifluoromethylsulfonyloxyphenyl)-5-estren-17-one a) 1.74 g of 3,3-(ethylenedioxy)-11β-(4-hydroxyphenyl)-5-estren-17-one is dissolved under protective gas together with 2.6 g of 4-dimethylaminopyridine in 42 ml of absolute methylene chloride, cooled to −78° C. and mixed with 0.94 ml of trifluoromethanesulfonic acid anhydride dissolved in 6 ml of absolute methylene chloride. After one more hour of stirring, the reaction mixture is poured on saturated sodium bicarbonate solution and the aqueous phase is extracted several times with methylene chloride. The combined organic phases are washed with saturated sodium chloride solution, dried on sodium sulfate and concentrated by evaporation in a vacuum. The residue is chromatographed on silica gel with a mixture of ethyl acetate/hexane and 1.81 g of 3,3-(ethylenedioxy)-11β-(4-trifluoromethylsulfonyloxyphenyl)-5-estren-17-one is obtained.

Melting point=208°-210° C. (diisopropyl ether); $[\alpha]_D^{20} = +73°$ (CHCl$_3$; c=0.51)

b) Analogously to the instructions for the triflate formation, 3.1 g of 3,3;17,17-bis-(ethylenedioxy)-11β-(4-trifluoromethylsulfonyloxyphenyl)-5-estrene is obtained as white foam from 3 g of 3,3;17,17-bis-(ethylenedioxy)-11β-(4-hydroxyphenyl)-5-estrene.

Melting point=91°-93° C. (methanol); $[\alpha]_D^{20} = +2°$ (CHCl$_3$; c=0.51)

Analogously to the above instructions for selective ketal cleavage, 2.1 g of 3,3-(ethylenedioxy)-11β-(4-trifluoromethylsulfonyloxyphenyl)-5-estren-17-one is obtained as white foam from 3 g of 3,3;17,17-bis-(ethylenedioxy)-11β-(4-hydroxyphenyl)-5-estrene.

3,3-(Ethylenedioxy)-11β-[[[4-(nonafluorobutyl)sulfonyl]oxy]phenyl]-5-estren-17-one 1 g of 3,3;17,17-bis-(ethylenedioxy)-11β-(4-hydroxyphenyl)-5-estrene is stirred with 1.9 g of 4-(dimethylamino)pyridine and 2.4 ml of nonafluorobutanesulfonyl fluoride in 40 ml of dichloromethane under protective gas for two days at room temperature. Then, the reaction mixture is poured on saturated sodium bicarbonate solution and the aqueous phase is extracted several times with methylene chloride. The combined organic phases are washed with water, dried on sodium sulfate and concentrated by evaporation in a vacuum. The residue is chromatographed on silica gel with a mixture of ethyl acetate/hexane and 1.26 g of the title compound is obtained.

Melting point=131° C. (methanol); $[\alpha]_D^{20} = +2°$ (CHCl$_3$; c=0.52)

3,3-(Ethylenedioxy)-11β-(4-vinylphenyl)-5-estren-17-one 1.7 g of 3,3-(ethylenedioxy)-11β-(4-trifluoromethylsulfonyloxyphenyl)-5-estren-17-one is dissolved in 25 ml of absolute dimethylformamide and mixed with 270 mg of lithium chloride and 190 mg of tetrakistriphenylphosphinepalladium. After five more minutes of stirring, the reaction mixture is mixed with 1.15 ml of tributylvinyltin, stirred for 1 hour at 110° C. under protective gas, cooled to room temperature and diluted with ethyl acetate. After filtration on Celite and washing of the filter residue with ethyl acetate, the organic phase is washed with saturated sodium chloride solution, dried on sodium sulfate and concentrated by evaporation in a vacuum. Chromatography of the residue on aluminum oxide (neutral, stage II) with a mixture of ethyl acetate/hexane yields 1.2 g of 3,3-(ethylenedioxy)-11β-(4-vinylphenyl)-5-estren-17-one as white foam.

3,3-(Ethylenedioxy)-11β-(4-tributylstannylphenyl)-5-estren-17-one 17.89 g of 3,3-(ethylenedioxy)-11β-(4-trifluoromethylsulfonyloxyphenyl)-5-estren-17-one is dissolved in 1.27 l of absolute dioxane and mixed with 5.4 g of lithium chloride and 2.95 g of tetrakistriphenylphosphinepalladium. After five more minutes of stirring, the reaction mixture is mixed with 33.1 ml of hexabutylditin, stirred for 2.5 hours at reflux under protective gas, cooled to room temperature and diluted with ethyl acetate. After filtration on Celite and washing of the filter residue with ethyl acetate, the organic phase is washed with saturated sodium chloride solution, dried on sodium sulfate and concentrated by evaporation in a vacuum. Chromatography of the residue on silica gel with a mixture of ethyl acetate/hexane yields 14.4 g of 3,3-(ethylenedioxy)-11β-(4-tributylstannylphenyl)-5-estren-17-one as white foam.

3,3-(Ethylenedioxy)-11β-[4-(3-pyridyl)phenyl]-5-estren-17-one 4.92 g (9.1 mmol) of 3,3-(ethylenedioxy)-11β-(4-trifluoromethylsulfonyloxyphenyl)-5-estren-17-one is dissolved in a mixture of 80 ml of toluene and 35 ml of ethanol and mixed in succession with 0.53 g of palladiumtetrakistriphenylphosphine, 0.77 g of lithium chloride, 11 ml of 2 molar sodium carbonate solution and 1.47 g (10 mmol) of diethyl(3-pyridyl)borane. The reaction mixture is then stirred for one hour at 110° C., cooled to room temperature and mixed with saturated sodium chloride solution. The organic phase is separated, washed in succession with 5% sodium hydroxide solution and water, washed on sodium sulfate and concentrated by evaporation in a vacuum. The residue is chromatographed on silica gel with a mixture of ethyl acetate/hexane. 3.55 g of 3,3-(ethylenedioxy)-11-[4-(3-pyridyl)phenyl]-5-estren-17-one and 382 mg of 3,3-(ethylenedioxy)-11-(4-ethylphenyl)-5-estren-17-one are obtained as white foams.

3,3-(Ethylenedioxy)-11β-[4-(2-thienyl)phenyl]-5-estren-17-one 3.3 ml of a 1.6 molar solution of butyllithium in hexane is slowly instilled in a solution of 423 μl of thiophene in 8 ml of tetrahydrofuran at room temperature under protective gas. After 30 more minutes of stirring, 872 mg of dry zinc(II) chloride, dissolved in 5 ml of diethyl ether, is added to the reaction mixture and stirred for one hour at room temperature. The thus produced 2-thienylzinc chloride solution is instilled in a solution of 480 mg of 3,3-(ethylenedioxy)-11β-(4-trifluoromethylsulfonyloxyphenyl)-5-estren-17-one and 51 mg of tetrakistriphenylphosphinepalladium in 10 ml of tetrahydrofuran. The reaction mixture is stirred for eight hours under reflux, cooled to room temperature and mixed with saturated ammonium chloride solution. The aqueous phase is extracted three times with ethyl acetate. The organic phases are washed with saturated sodium chloride solution, dried on sodium sulfate and concentrated by evaporation in a vacuum. Chromatography of the residue on silica gel with a mixture of ethyl acetate/hexane yields 380 mg of the title compound as white foam.

3,3-(Ethylenedioxy)-11β-[4'-(methylthio)[1,1'-biphenyl]-4-yl]-5-estren-17-one 1.73 g of 3,3-(ethylenedioxy)-11β-(4-trifluoromethylsulfonyloxyphenyl)-5-estren-17-one is dissolved in a mixture of 17 ml of toluene and 5 ml of ethanol and mixed in succession with 37 mg of palladiumtetrakistriphenylphosphine, 0.28 mg of lithium chloride, 4 ml of 2 m sodium carbonate solution and 0.7 g of [4-(methylthio)phenyl]boronic acid. The reaction mixture is then stirred for 6 hours at 95° C., cooled to room temperature and mixed with saturated sodium chloride solution. The organic phase is separated, washed in succession with 5% sodium hydroxide solution and water, dried on sodium sulfate and concentrated by evaporation in a vacuum. The residue is chromatographed on silica gel with a mixture of ethyl acetate/hexane. 1.65 g of the title compound is obtained as white foam.

Corresponding to the table below, other products can also be produced analogously to the five above-named instructions:

| Aromatic compound | Product | Yield % | Physical Data |
| --- | --- | --- | --- |
| tri-n-butyl-vinyltin | 3,3-ethylenedioxy-11β-(4-vinylphenyl)-5-estren-17-one | 91 | mp = > 330° C. decomposition (diisopropyl ether) $[\alpha]_D^{20} = +96°$ (CHCl$_3$; c = 0.5) |
| tri-n-butyl-3-furyltin | 3,3-ethylenedioxy-11β-[4-(3-furyl)-phenyl]-5-estren-17-one | 82 | mp = 204° C. (diisopropyl ether) $[\alpha]_D^{20} = +83°$ (CHCl$_3$; c = 0.515) |
| diethyl-3-pyridyl-borane | 3,3-ethylenedioxy-11β-[4-(3-pyridyl)-phenyl]-5-estren-17-one | 83 | MP = 133° C. (ethyl acetate) $[\alpha]_D^{20} = +73°$ (CHCl$_3$; c = 0.5) |
| | 3,3-ethylenedioxy-11β-(4-ethylphenyl)-5-estren-17-one | 10 | mp = 173° C. (diisopropyl ether) $[\alpha]_D^{20} = +94°$ (CHCl$_3$; c = 0.5) |
| Diethyl-5-pyrimidinyl-borane | 3,3-ethylenedioxy-11β-[4-(5-pyrimidinyl)-phenyl]-5-estren-17-one | 73 | mp = 212° C. (ethyl acetate/hexane) $[\alpha]_D^{20} = +75°$ (CHCl$_3$; c = 0.5) |
| | 3,3-ethylenedioxy-11β-(4-ethylphenyl)-5- | 8 | |

| Aromatic compound | Product | Yield % | Physical Data |
|---|---|---|---|
| hexabutyldi-tin | estren-17-one 3,3-ethylenedioxy-11β-(4-tri-n-butylstannyl-phenyl)-5-estren-17-one | 64 | $^1$H-NMR (CDCl$_3$) δ [ppm]: 7.25–7.35 (4H,m,H-aromatic); 5.57 (1H,m,H-6); 3.44 (1h,tr J=5.5Hz broad,H-11); 0.85 (3H,tr J=7.5Hz,H-CH$_3$); 0.55 (3H, s, H-18) |
| 2-thienyl-zinc chloride | 3,3-ethylenedioxy-11β-[4-(2-thienyl)phenyl]-5-estren-17-one | 90 | mp = 214° C. (ethyl acetate/hexane) $[α]_D^{20}$ = +76° (CHCl$_3$; c = 0.5) |
| 2-benzo-furanylzinc chloride | 11β-[4-(2-benzofuranyl)-phenyl]-3,3-ethylene-dioxy-5-estren-17-one | 91 | $^1$H-NMR (CDCl$_3$) δ [ppm]: 7.77 (2H,d J=9Hz,H-aromatic); 7.59–7.20 (4H,m,H-benzofuranyl); 7.45 (2H,d J=9Hz,H-aromatic); 7.00 (1H,s,H-furanyl); 5.59 (1H,m,H-6); 3.52 (1H,t broad, J=5.5Hz,H-11); 0.63 (1H,s,H-18) |
| (5-ethyl-2-thienyl)-tributyl-stannane | 3,3-ethylenedioxy-11β-[4-(5-ethyl-2-thienyl)-phenyl]-5-estren-17-one | 70 | mp = 192° C. (ethyl acetate/diisopropyl ether) $[α]_D^{20}$ = +71° (CHCl$_3$); c = 0.5) |
| [4-(methyl-thio)phenyl] boronic acid | 3,3-ethylenedioxy-11β-[4'-(methylthio)[1,1'-biphenyl]-4-yl]-5-estren-17-one | 69 | mp = 226° C. (hexane/ethyl acetate) IR (KBr) 1740 cm$^{-1}$ (C=O) |
| [4-(di-methyl-amino)-phenyl]-boronic acid | 11β-[4'-(dimethyl-amino)[1,1'-biphenyl]-4-yl]-3,3-ethylenedioxy-5-estren-17-one | 58 | $^1$H-NMR (CDCl$_3$) δ [ppm]: 7.51(2H,d J=9Hz,H-aromatic); 7.46 (2H,d J=9Hz,H-aromatic); 7.37 (2H, d J=9Hz,H-aromatic); 6.80 (2H,d J=9Hz,H-aromatic); 5.59 (1H,m,H-6); 3.50 (1H,t broad J=5.5Hz,H-11); 3.00 (6H, s, H-NMe$_2$) ;0.63 (3H,s,H-18) |
| [4-(2-methyl-1,3-dioxolan-yl)phenyl]-boronic acid | 3,3-ethylenedioxy-11β-[4'-(2-methyl-1,3-dioxolan-2-yl)[1,1'-biphenyl]-4-yl]-5-estren-17-one | 82 | 1H-NMR (CDCl$_3$) δ [ppm]: 7.59 (2H,d J=9Hz,H-aromatic); 7.55 (2H,d J=9Hz,H-aromatic); 7.50 (2H,d J=9Hz,H-aromatic); 7.42 (2H,d J=9Hz,H-aromatic); 5.60 (1H,m,H-6); 3.52 (1H, t broad J=5.5Hz,H-11); 1.70 (3H,s,H-methyl); 0.632 (3H,s,H-18) |

3,3-(Ethylenedioxy)-17-cyanomethyl-11β-[4-(3-pyridyl)phenyl]-5-estren-17β-ol 13.7 ml of a 1.6 n n-butyllithium solution in hexane is instilled in a solution of 3.31 ml of diisopropylamine in 100 ml of absolute tetrahydrofuran at −78° C. under protective gas. After 30 minutes, 1.13 ml of acetonitrile is added at the same temperature. 15 minutes later, a solution of 1 g of 3,3-(ethylenedioxy)-11β-[4-(3-pyridyl)phenyl]-5-estren-17-one in 90 ml of absolute tetrahydrofuran is instilled at the same temperature and stirred for another two hours. Then, it is mixed with saturated ammonium chloride solution and extracted with ethyl acetate. The combined organic phases are washed with saturated sodium chloride solution, dried on sodium sulfate and concentrated by evaporation in a vacuum. Chromatography of the residue on silica gel with a mixture of ethyl acetate/hexane yields 0.95 g of 3,3-(ethylenedioxy)-17-cyanomethyl-11β-[4-(3-pyridyl)phenyl]-5-estren-17β-ol as white foam.

IR (KBr): 2250 cm$^{-1}$

17β-Hydroxy-17-cyanomethyl-11β-[4-(3-pyridyl)-phenyl]-4-estren-3-one

Analogously to the above instructions for ketal cleavage, 0.63 g of 17β-hydroxy-17-cyanomethyl-11β-[4-(3-pyridyl)phenyl]-4-estren-3-one is obtained as white foam from 0.9 g of 3,3-(ethylenedioxy)-17-cyanomethyl-11β-[4-(3-pyridyl)phenyl]-5-estren-17β-ol.

Melting point=173°-174° C.; [α]$_D^{20}$=+132° (CHCl$_3$; c=0.5)

3,3-(Ethylenedioxy)-11β-[4'-(methylsulfinyl)[1,1'-biphenyl]-4-yl]-5-estren-17-one 494 mg of 3,3-(ethylenedioxy)-11β-[4'-(methylthio)[1,1'-biphenyl]-4-yl]-5-estren-17-one is dissolved in a mixture of 6 ml of tetrahydrofuran, 6 ml of methanol and 2 ml of water and mixed with 924 mg of sodium periodate. The reaction mixture is stirred at room temperature overnight, then filtered on Celite and the filtrate is diluted with ethyl acetate. The organic phase is washed with saturated sodium bicarbonate solution, dried on sodium sulfate and concentrated by evaporation in a vacuum. After chromatography of the residue on silica gel with a mixture of hexane/ethyl acetate, 346 mg of the title compound is obtained as white foam.

IR (KBr): 1736 cm$^{-1}$ (C=O)

It is claimed:

1. A process for the production of 10β-H-11β-(substituted phenyl) steroids of formula Ia

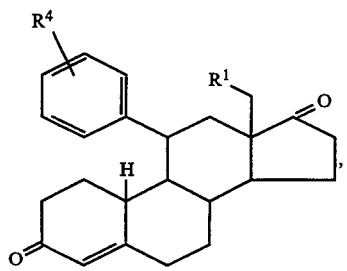

or of formula Ib

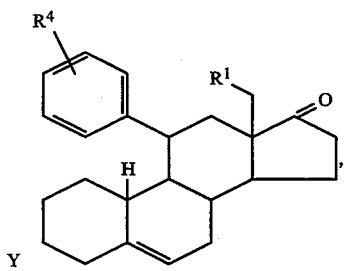

in which
R$^4$ stands for a hydrogen atom, a cyano group, a chlorine atom, a fluorine atom, a bromine atom, an iodine atom, a trialkylsilyl group, a trialkylstannyl group, a straight-chain or branched, saturated or unsaturated C$_1$-C$_8$ alkyl group, an optionally protected acyl or alkoxyalkyl radical, an amino group

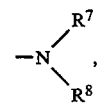

in which R$^7$ and R$^8$, independent of one another, mean a hydrogen atom or a C$_1$-C$_4$ alkyl group, or a corresponding amine oxide

a group —OR$^9$ or —S(O)$_i$R$^9$ where i=0, 1 or 2, in which R$^9$ means a hydrogen atom, or a methyl, ethyl, propyl, isopropyl, methoxyphenyl, allyl or 2-dimethylaminoethyl group, a heteroaryl radical of the formula Iα

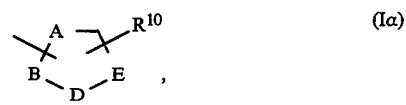

in which A is a nitrogen, oxygen or sulfur atom, -B-D-E is the element sequence —C—C—C—, —N—C—C— or —C—N—C and
R$^{10}$ is a hydrogen atom, a cyano group, a chlorine atom, a fluorine atom, a bromine atom, an iodine atom, a trialkylsilyl group, a trialkylstannyl group, a straight-chain or branched, saturated or unsaturated C$_1$-C$_8$ alkyl group, an optionally protected acyl or alkoxyalkyl radical, an amino group

in which R$^7$ and R$^8$, independent of one another, mean a hydrogen atom or a C$_1$-C$_4$ alkyl group, or a corresponding amine oxide

or a group OR$^9$ or —S(O)$_i$R$^9$ where i=0, 1 or 2, in which R$^9$ means a hydrogen atom, or a methyl, ethyl, propyl, isopropyl, methoxyphenyl, allyl or 2-dimethylaminoethyl group,
a heteroaryl radical of formula Iβ

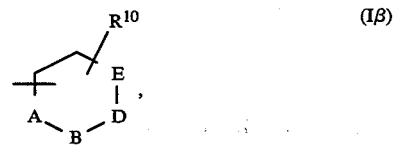

in which A means a nitrogen atom and -B-D-E means the element sequence —C—C—C, —N—C—C, —C—N—C or —C—C—N and R$^{10}$ has the already indicated meaning, or a phenyl radical of formula Iγ

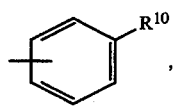 (Iγ)

in which R$^{10}$ has the already indicated meaning, Y means a protected keto group or a protected hydroxy group and a hydrogen atom, and
R$^1$ means a hydrogen atom or a methyl group, which comprises stereoselectively reducing a compound of formula III

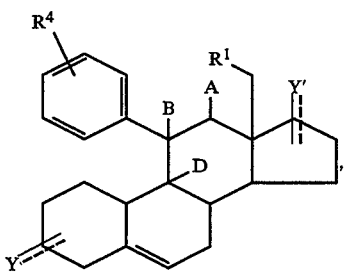 (III)

in which
A and B together mean an additional bond, and
D means a hydrogen atom or
B and D together mean an additional bond and
A means a hydrogen atom and
R$^4$, Y and R$^1$ have the meaning indicated in formulas Ia or Ib and Y' independently has the same meaning as Y with an electropositive metal in an electron-solvating solvent to stereoselectively produce the 11β stereoisomer of a 11β-(substituted phenyl) compound of formula IIa

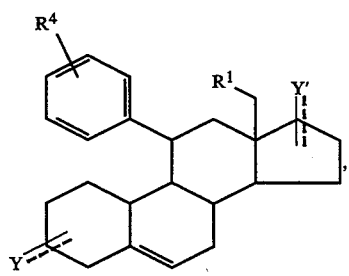 (IIa)

in which R$^4$, Y, Y' and R$^1$ have the already indicated meaning and then optionally this compound of formula II is cleaved either with hydrochloric acid, sulfuric acid, phosphoric acid, toluenesulfonic acid or another strong mineral acid to a compound of formula Ia or partially cleaved with acetic acid, oxalic acid or another organic acid to a compound of formula Ib.

2. A process according to claim 1, wherein the reduction is performed with lithium, sodium, potassium, calcium as electropositive metal.

3. A process according to claim 2, wherein the reduction is performed with lithium in liquid ammonia, as the electron-solvating solvent.

4. A process according to claim 1, wherein the reduction is performed with an excess of the electropositive metal.

5. 11β-(substituted phenyl) compounds of the formula Ib

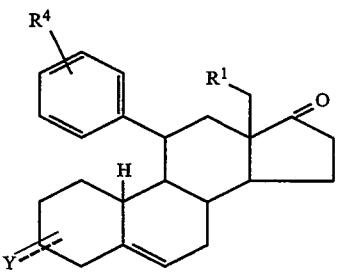 (Ib)

and of the formula Ia

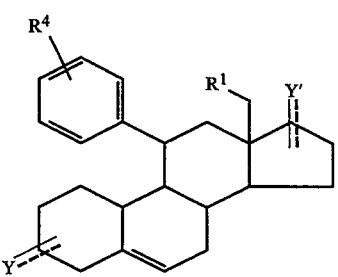 (IIa)

in which
R$^4$ stands for a hydrogen atom, a cyano group, a chlorine atom, a fluorine atom, a bromine atom, an iodine atom, a trialkylsilyl group, a trialkylstannyl group, a straight-chain or branched, saturated or unsaturated C$_1$-C$_8$ alkyl group, an optionally protected acyl or alkoxyalkyl radical, an amino group

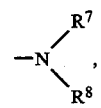

in which R$^7$ and R$^8$, independent of one another, mean a hydrogen atom or a C$_1$-C$_4$ alkyl group, or a corresponding amine oxide

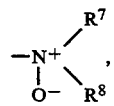

a group —OR$^9$ or —S(O)$_i$R$^9$ where i=0 1 or 2, in which R$^9$ means a hydrogen atom, or a methyl, ethyl, propyl, isopropyl, methoxyphenyl, allyl or 2-dimethylaminoethyl group, a heteroaryl radical of the formula Iα

 (Iα)

in which A is a nitrogen, oxygen or sulfur atom, -B-D-E is the element sequence —C—C—C—, —N—C—C— or —C—N—C and
R$^{10}$ is a hydrogen atom, a cyano group, a chlorine atom, a fluorine atom, a bromine atom, an iodine atom, a trialkylsilyl group, a trialkylstannyl group, a straight-chain or branched, saturated or unsaturated $C_1$-$C_8$ alkyl group, an optionally protected acyl or alkoxyalkyl radical, an amino group

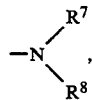

in which $R^7$ and $R^8$, independent of one another, mean a hydrogen atom or a $C_1$-$C_4$ alkyl group, or a corresponding amine oxide

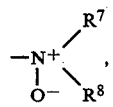

or a group —$OR^9$ or —$S(O)_iR^9$ where i=0, 1 or 2, in which $R^9$ means a hydrogen atom, or a methyl, ethyl, propyl, isopropyl, methoxyphenyl, allyl or 2-dimethylaminoethyl group, a heteroaryl radical of formula Iβ

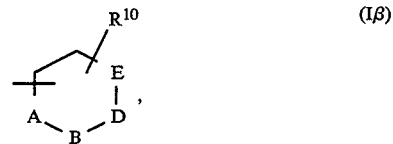

in which A means a nitrogen atom and -B-D-E means the element sequence —C—C—C, —N—C—C, —C—N—C or —C—C—N and $R^{10}$ has the already indicated meaning, or a phenyl radical of formula Iγ

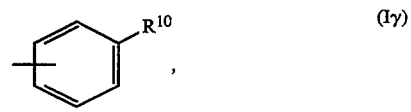

in which $R^{10}$ has the already indicated meaning,
Y means a protected keto group or a protected hydroxy group and a hydrogen atom, and
$R^1$ means a hydrogen atom or a methyl group.

* * * * *